United States Patent [19]

Nelson et al.

[11] Patent Number: 4,948,974

[45] Date of Patent: Aug. 14, 1990

[54] HIGH RESOLUTION IMAGING APPARATUS AND METHOD FOR APPROXIMATING SCATTERING EFFECTS

[76] Inventors: Robert S. Nelson, 2922 Upshur St., San Diego, Calif. 92106; D. Zach Reuven, 27572 Santa Charita, Saugus, Calif. 91350

[21] Appl. No.: 221,648

[22] Filed: Jul. 20, 1988

Related U.S. Application Data

[63] Continuation-in-part of Ser. No. 22,283, Mar. 5, 1987, Pat. No. 4,829,184, which is a continuation-in-part of Ser. No. 624,467, Jun. 25, 1984, Pat. No. 4,649,275.

[51] Int. Cl.$^5$ ............................................. G01N 21/00
[52] U.S. Cl. ................................ 250/358.1; 128/664; 250/341
[58] Field of Search .................. 250/341, 360.1, 358.1; 128/665, 664

[56] References Cited

U.S. PATENT DOCUMENTS

| | | | |
|---|---|---|---|
| 4,515,165 | 5/1985 | Carroll | 128/664 |
| 4,649,275 | 3/1987 | Nelson et al. | 250/358.1 |
| 4,767,928 | 8/1988 | Nelson et al. | 250/341 |
| 4,807,637 | 2/1989 | Bjorkholm | 128/664 |
| 4,810,875 | 3/1989 | Wyatt | 250/227 |

*Primary Examiner*—Constantine Hannaher
*Attorney, Agent, or Firm*—Lyon & Lyon

[57] ABSTRACT

A source of high resolution non-ionizing radiation of narrow spectral bandwidth is used in conjuction with optical detectors positioned on one or more sides of a breast to obtain mammographic images. Reflected and transmitted images may be obtained to determine the position of objects within the breast and their nature. The magnitude of multiple scattered coaxial radiation may also be determined.

Focused light can be use to acquire tomographic image slices of the breast in reflection and transmission imaging modes.

10 Claims, 7 Drawing Sheets

RASTER SCAN FORMAT INCIDENT
NORMAL TO SURFACE

MULTIPLE RASTER SCAN

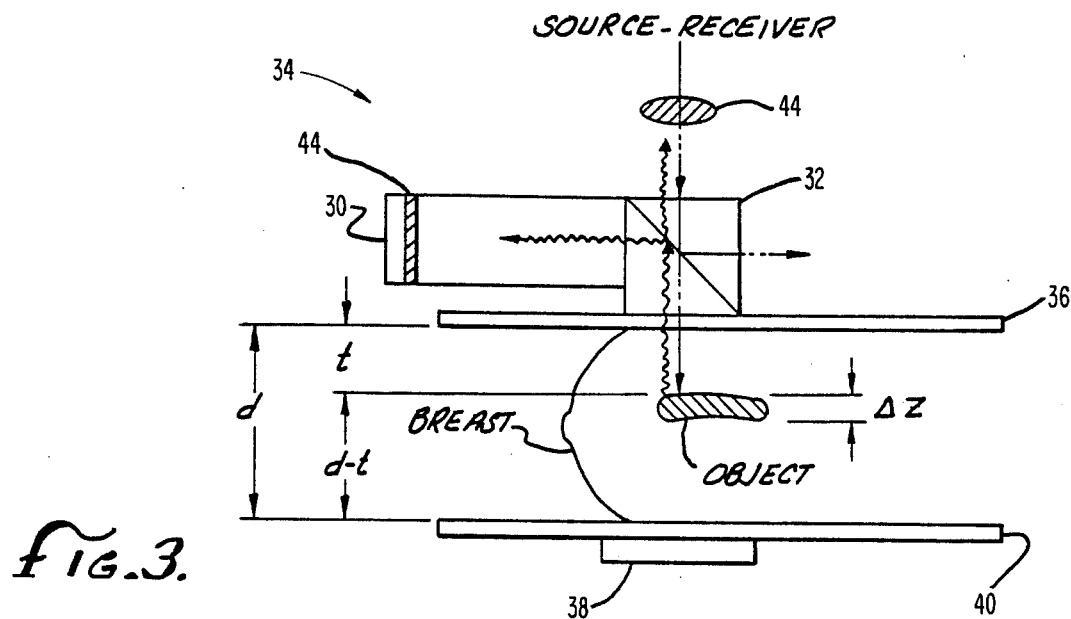
fig.3.
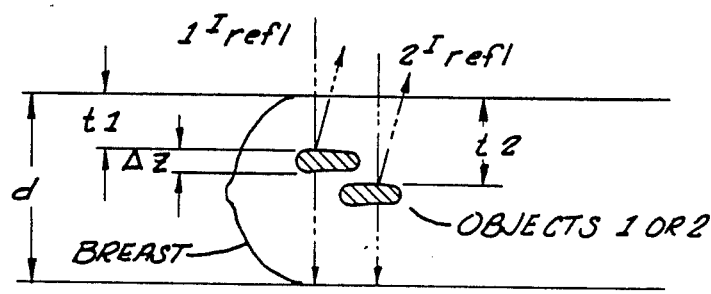
fig.4a.
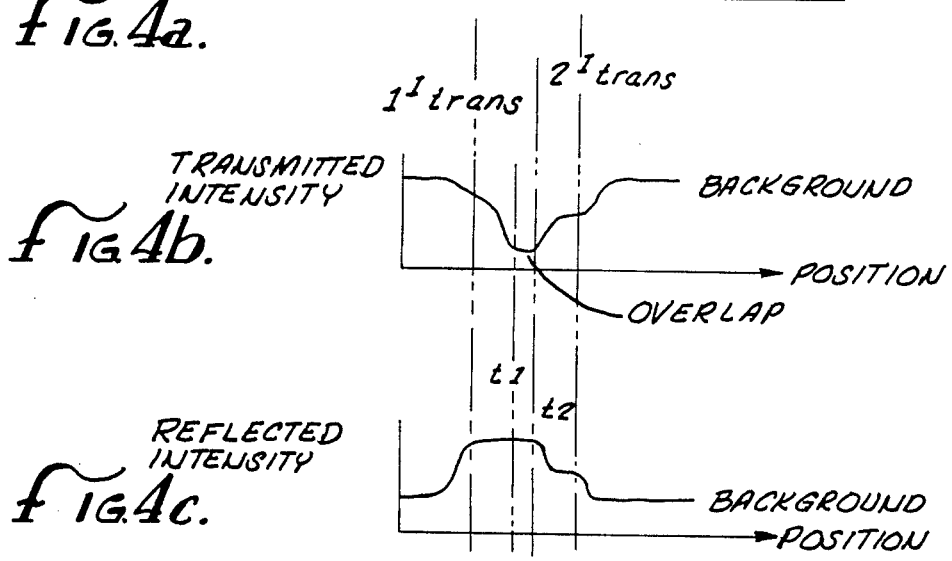
fig.4b.
fig.4c.

HIGH RESOLUTION IMAGING APPARATUS AND METHOD FOR APPROXIMATING SCATTERING EFFECTS

RELATED APPLICATIONS

This application is a continuation-in-part of Ser. No. 022,283, filed Mar. 5, 1987, now U.S. Pat. No. 4,829,184 which is a continuation-in-part of Ser. No. 624,467 filed June 25, 1984 now U.S. Pat. No. 4,649,275.

BACKGROUND OF THE INVENTION

X-ray mammography based on film-screen or xeroradiographic detection is commonly accepted as a mass screening technique for breast disease. However, certain risks are associated with x-ray examination because x-ray radiation is also ionizing. The possibility of genetic damage and radiation-induced cancer limits the recommended age group to older women as well as the frequency of exams.

More recently, broad beam light sources (sometimes referred to as "light torches") with a wide spectral bandwidth in the visible and infrared range have been used for breast imaging. The broad beam transmitted through the breast is usually recorded by a video camera, converted to an analog signal and viewed on a video monitor, or is digitized and analyzed on a computer. The ability to discriminate between various tissue-types in the breast, however, is reduced if the transmitted beam has a wide spectral bandwidth. Lesions that absorb, transmit, scatter, or reflect light to different degrees in comparison with normal tissue may exhibit reduced contrast. Moreover, the transmitted beam measurement includes the combined effects of absorption, reflection, and scattering. If a structure is highly reflective rather than strongly absorptive, the transmission measurement will not identify that property. It is thus very difficult to obtain information about the nature of the object, i.e., whether the object is a cyst, a tumor, a calcium deposit, etc.

Spatial resolution and contrast is also lost because a large amount of scattered light is transmitted from the breast to the detector. Also, structures nearest to the exit surface will cast more distinct shadows than objects close to the entrance surface. Lesion sizes that are detectable with this approach have generally been no smaller than what the physician can detect by palpation. Resolution is far below that which can be obtained with x-ray imaging systems.

Further limitations associated with measuring a transmitted beam are related to the position of objects along the beam path. Positional information of light attenuating objects is difficult to obtain because only the transmitted beam intensity is measured. If two objects obscure the beam, permitting only a weak beam to be transmitted, it is difficult to distinguish between them. Reversing the positions of the source and detector generates the same signal because the attenuating path remains the same. It is thus difficult to discern between one, two or more objects in the beam path.

SUMMARY OF THE INVENTION

The present invention is directed to a non-ionizing radiation imaging system for mammography. To this end, a source of non-ionizing radiation of narrow spectral bandwidth is used to produce a beam or a number of beams to be directed toward a breast. Optical detectors positioned on one or more sides of the breast are used to obtain high resolution images of radiation reflected from or transmitted through objects within the breast, or both. Means may be provided to determine the effects of multiple scattered radiation. In this manner, improved image acquisition, object position and tissue-type data may be obtained.

BRIEF DESCRIPTION OF THE DRAWINGS

FIG. 3 shows an arrangement as in FIG. 1 for the imaging of reflected and transmitted light using a beam splitter. Polarizers are also shown adjacent the source and the reflected radiation detector.

FIG. 4 [parts (a), (b) and (c)] shows how transmitted and reflected imaging signals can be used to obtain positional information.

DETAILED DESCRIPTION OF PREFERRED EMBODIMENTS

Figure 1A:
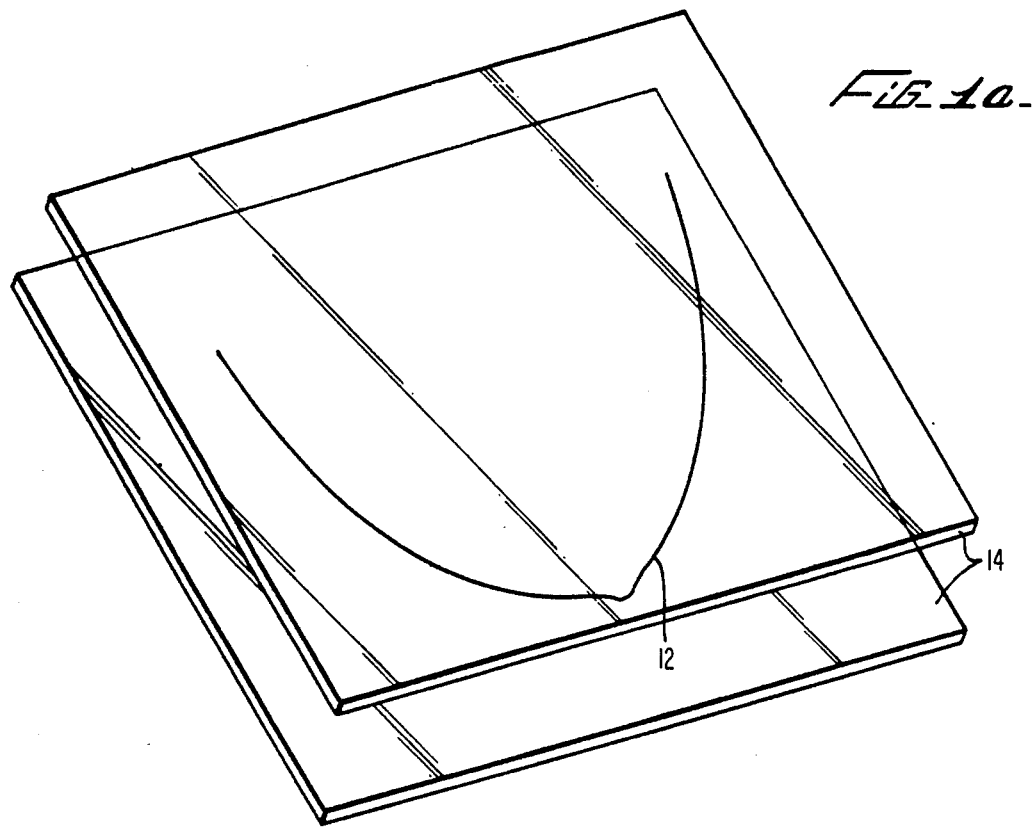
FIG. 1(a) shows a breast in a compressed position between two transparent plates. These "compression" plates are transparent to the light wavelengths that would be used in imaging the breast. For illustrative purposes, the size of these plates is similar to those used in conventional x-ray mammography. Plate size can be reduced to permit imaging of small sections of a breast.

FIGS. 1 and 2 depict apparatus for mammographic (breast imaging) applications which entail using light of narrow spectral bandwidth (near ultraviolet, visible or infrared) to obtain high resolution images. Appropriate narrow spectral bandwidth sources of light include lasers or filtered light sources. The light source is positioned on one side of the breast. A photodetector positioned on the opposite side of the breast records the transmitted light. Resolution is controlled by adjusting the area of the light beam(s) before and/or after transmission through the breast. Collimation introduced before the photodetector reduces the level of scattered light. The photodetector produces an analog signal which can be displayed or digitized for storage and analysis by a computer.

The breast often has an irregular shape. To reduce problems associated with light incident on and transmitted out of surfaces which are not necessarily normal to the direction of beam transmission, it is desirable to flatten the entrance and exit breast surfaces. This is easily accomplished using a pair of transparent flat compression plates. The optical path length can also be reduced by physically compressing the breast or a region thereof.

Figure 1B:
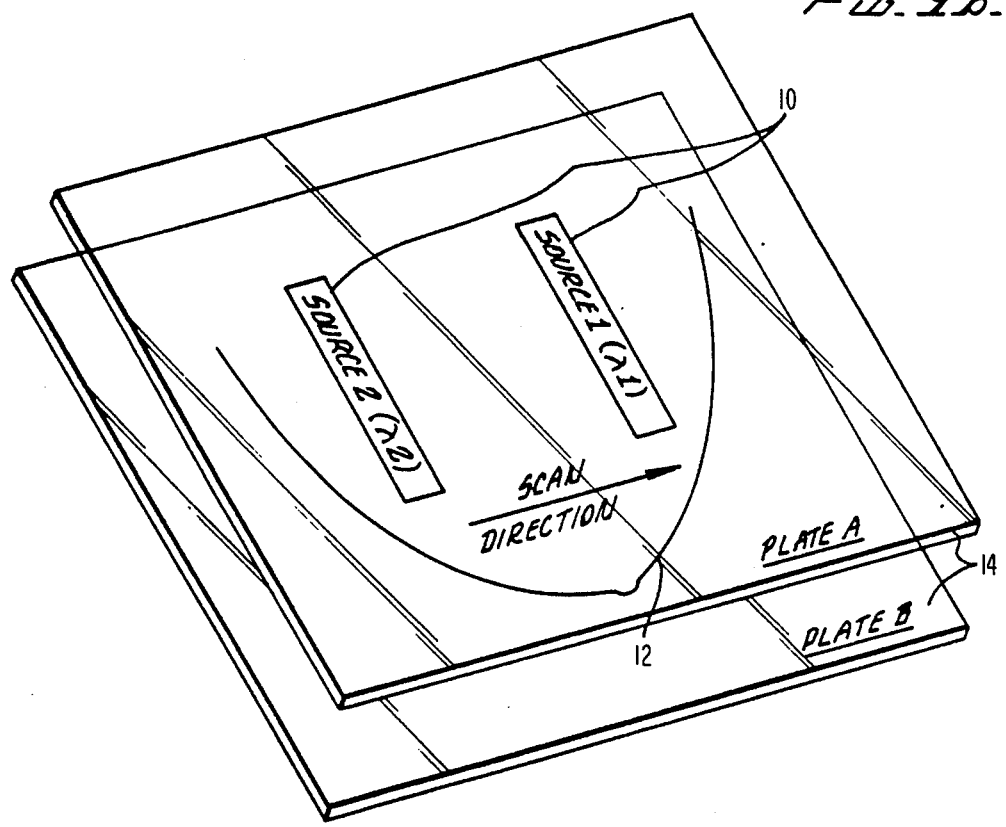
FIG. 1(b) shows the arrangement of FIG. 1 wherein one, two or more point, line or two-dimensional sources, each source emitting collimated light of a distinct wave length is (are) moved parallel to the surface of a compression plate. A detector corresponding to each source moves in synchronism with the source parallel to the surface of the second plate. Analog signals from the detector(s) can be digitized and stored in computer memory for display, processing and analysis purposes.

As can be appreciated from FIG. 1(b), light beams of wave length $\lambda_1$ and $\lambda_2$ sent from sources 1 and 2 are incident normal to the surface of one compression plate. The transmitted light is attenuated by the two plates and the breast material. An image or images can be acquired by simultaneously translating one or more plate source-light detector combinations past the breast. Each light source emits a different wavelength (e.g., $\lambda_1$ and $\lambda_2$ as shown in FIG. 1(b)).

Figure 2A:
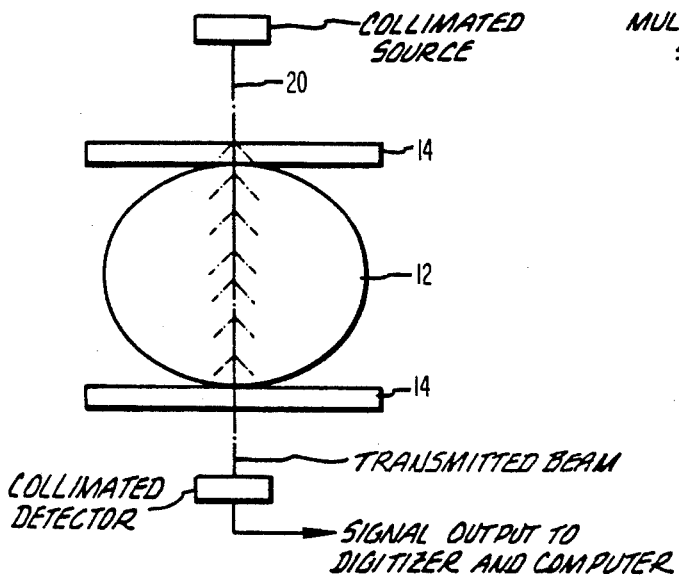
FIG. 2(a) shows a collimated pencil beam from a point source used in a raster format. The detector may use additional collimation to help minimize detection of scattered light. Collimation techniques for scatter reduction may include air-gaps, mechanical apertures such as grids, fiber optics or light pipes.
Figure 2B:
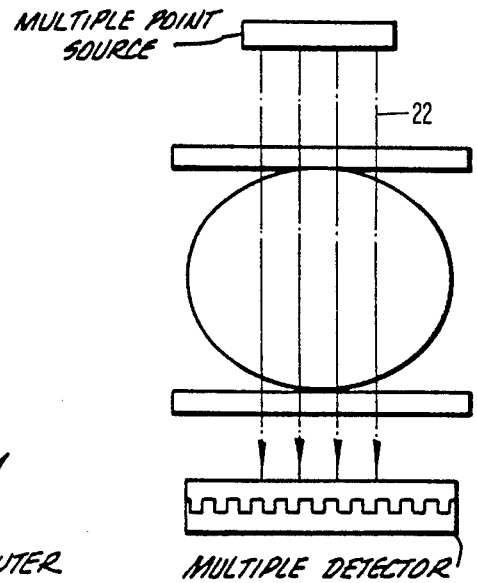
FIG. 2(b) shows multiple point beams used in a raster scan format to reduce image acquisition time.
Figure 2C:
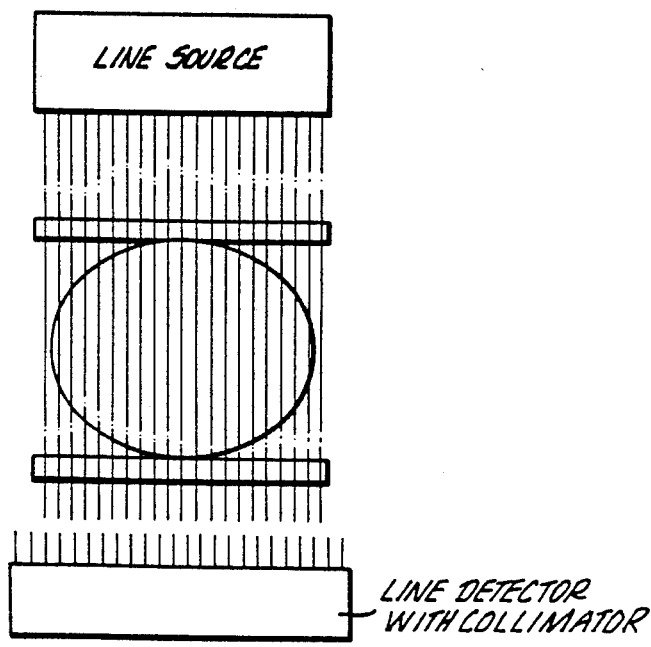
FIG. 2(c) shows a collimated (single or multiple) line beam of light providing a line scanning format. The array of detectors would use some form of collimation to reduce detected light scatter from the subject.

High resolution images may be obtained with a variety of scanning techniques. FIGS. 2(a) and (b) show a point beam or a multiple point beam which could be used in a raster scan format. The transmitted light beam can be collimated by a simple air gap, fiber optics, light pipes or mechanical apertures to minimize detection of scattered light. This approach can be extended to include a single line or a multiple line scanned format as shown in FIG. 2(c).

Figure 2D:
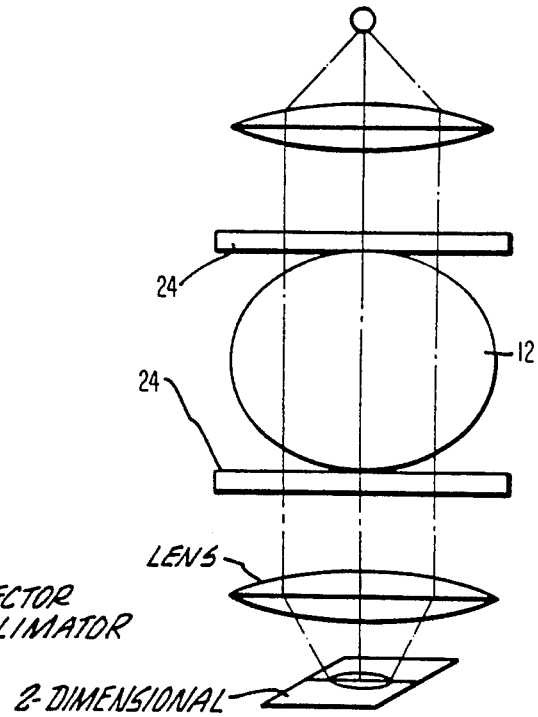
FIG. 2(d) shows a parallel light beam used for rapid image acquisition by a detector. In this case, the collimation is incorporated into the compression plates.

High speed two-dimensional imaging is shown in FIG. 2(d). In this case, collimation (such as fiber optics or light pipes) can be introduced into one or both compression plates.

In all cases collimation may be used to produce a beam or beams of very small cross section and a highly directional nature. This latter attribute can be used to exclude transmitted scatter from the exit beam. Since many versions of this invention are possible, light source requirements may range from a continuous to a rapidly pulsed source.

As shown in FIG. 3, an additional optical detector and a beam splitter may be positioned on the same side of the breast as the light source to form a source detector unit for recording light that is reflected from objects within the breast. In FIG. 3, the source-detector unit is disposed adjacent the top compression plate (plate A). The beam splitter allows some fraction of the light from the source to pass into the breast. The optical detector placed beneath the bottom compression plate (plate B) will receive an image created by the transmitted light. Some fraction of the light which is reflected back from objects within the breast will be directed by the beam splitter to the optical detector measuring reflected light. The signals generated by each optical detector are directed to a computer for composite or separate image analysis.

Although not shown in FIG. 3, an alternative arrangement would be to replace the simple detector beneath the bottom compression plate with a second source-detector unit. By multiplexing the two source-detector units, the upper source-detector unit could be used to measure a reflected beam at one instance and then measure a transmitted beam at the next instance.

To prevent interference from light which is reflected back from the surface of the breast, it is advantageous, although not necessary, to employ a pair of polarizing filters I and II which are typically rotated 90° from each other. The first polarizer is placed adjacent to the source, while the second polarizer is placed adjacent to the reflective optical detector. Because light reflected from the breast surface would largely have a direction of polarization similar to that of the polarized input source, the second polarizer (which is a cross-polarizer when rotated 90° to the first polarizer) will attenuate such surface reflected light. It is also possible to rotate the second polarizer over a range of angles, thereby permitting the reflected light to be analyzed as a function of degree of rotation. If desired, the polarizers may be positioned directly on the beam splitter itself. Moreover, the first optical detector may likewise be mounted directly on the beam splitter.

Use of an optical detector to measure reflected light yields several advantages. First, high resolution images of objects located between the source side of the breast and the midpoint between the compression plates can be obtained due to the reduction in light path length and consequent decrease in attenuation and scatter. By obtaining images on opposite sides of the breast, most of the objects within the breast can be viewed with greater clarity. Second, a detector measuring the reflected beam can be used to obtain tissue-type data through determination of the reflective-transmissive properties of objects within the breast. Third, a detector measuring the reflected beam can be used to obtain positional information of objects within the breast.

FIG. 4 illustrates the above advantages. As shown therein, for objects having position $t < d/2$, a reflected image can be obtained using a total light path length that is less than d. The approximate z value of the object, which is the distance from the top compression plate to the object, can be determined, as can its reflectivity, if reflected images are obtained on opposite sides of the breast.

In FIG. 4, the z values for two objects 1 and 2 are designated $t_1$ and $t_2$, respectively. By directing a light source at opposite sides of the breast, the respective intensities of the reflected light can be measured. The measured intensity will relate to incident optical intensity in accordance with the following formula:

$$I_{refl} \sim I_0 Q e^{-2tu} \text{ where:}$$

$I_{refl}$ = reflected optical intensity.
$I_0$ = incident optical intensity at the entrance surface;
t = actual depth of one surface of the object
u = optical attenuation coefficient of breast medium;
Q = reflectivity of the object;

If the thickness ($\Delta z$) of an object in the breast is small relative to breast thickness, i.e., $\Delta z << d$, the depth or z value of the object can be roughly estimated using the above equation. If Q and u remain the same for both measurements, and multiple reflections between the top and bottom surfaces of the object are ignored, then:

$$I_{refl}(top) \sim I_0 Q e^{-2tu} \text{ and}$$

$$I_{refl}(bottom) \sim I_0 Q e^{-2(d-t)u}$$

From these equations it is a simple matter of solving for the two unknowns t and Q to determine the z value and reflectivity of the object in question. If the object thickness, $\Delta z$, is not small, then a third measurement using reflected or transmitted light, could be made at 90 degrees to the other measurements to determine $\Delta z$. In some cases a transmission measurement from one of the first two image scans may be useful in estimating $\Delta z$, or at least whether the object is thick or not (i.e. was the estimated attenuation by the object small or large for the type of object expected). Thus, if u (optical attenuation coefficient of the object) is known, $\Delta z$ could be estimated by introducing a third equation for the transmitted beam:

$$I \sim I_0[1-Q]e^{-(d-\Delta z)u - \Delta z u'}$$

while modifying $I_{refl}(bottom) \sim I_0 Q e^{-2(d-t-\Delta z)u}$.
The three equations may be solved to find Q, t and $\Delta z$.

If two objects partially obscure each other and are not too close together, two reflection measurements as described above can be of help in distinguishing the objects. There may be some edge enhancement at the position of overlap of objects 1 and 2 due to double reflection. The reflected intensity pattern would be roughly reversed if measurements were taken with the detector receiver units placed on the opposite side of the breast.

Figure 5A:
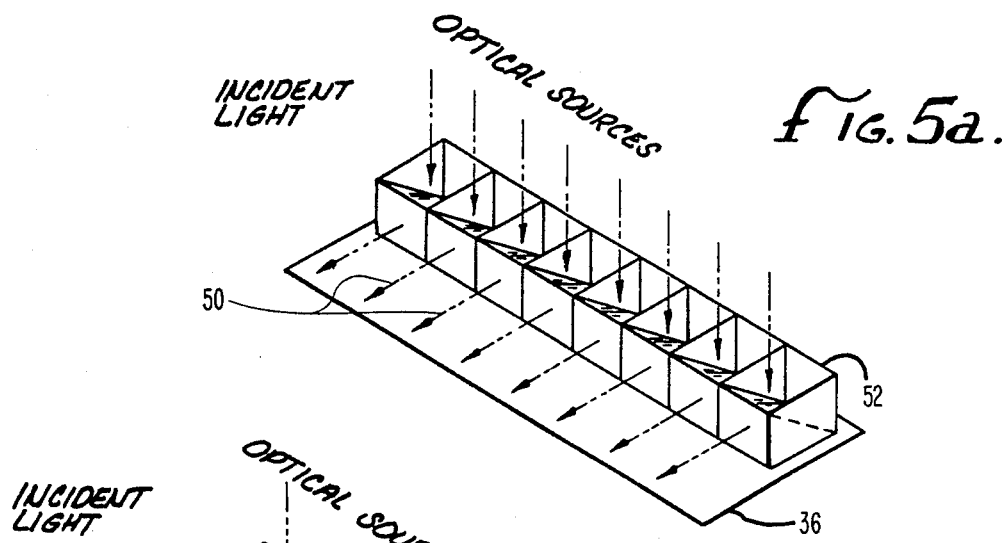
FIG. 5 [parts (a) and (b)] shows two beam splitter designs for use with a line radiation source.
Figure 5B:
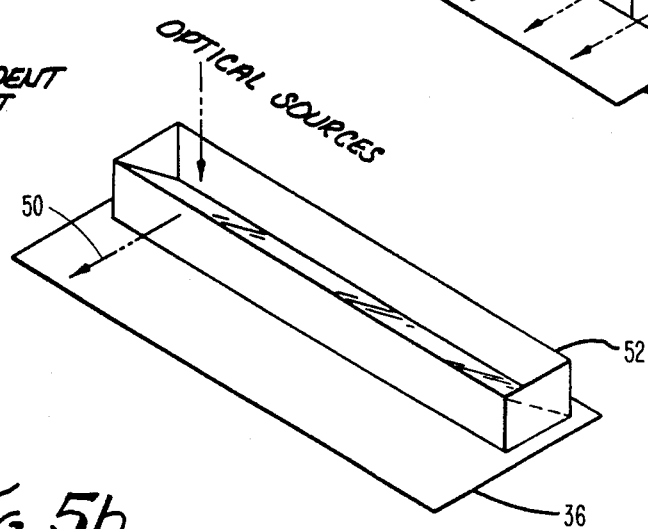

The beam splitter approach for detecting the reflected beam can be implemented in a linear or two-dimensional array as shown in FIG. 5. The reflected light passes through an optional polarizer, and is brought to an array of detectors (or a camera) with an optional polarizer by a collecting lens or light-pipes. Detectors can be mounted on the array directly. Mirrors can be introduced to alter the path further.

Figure 6:
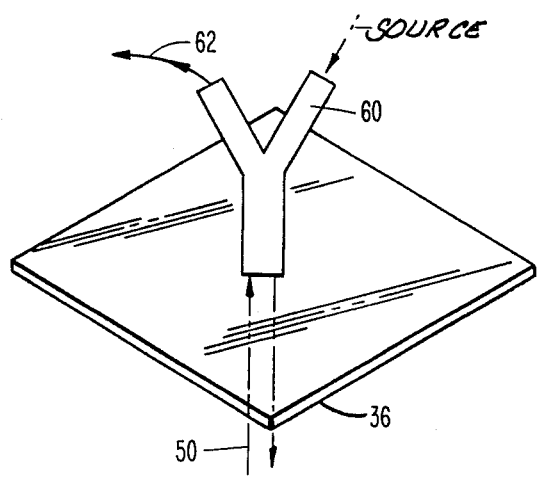
FIG. 6 shows a fiber optic "Y" coupler for use in a one- or two-dimensional array.

An alternative to the beam splitter arrangement shown in FIG. 5 is to use a fiber optic "Y" coupler or fiber splitter with or without polarizers for the input and reflected signal as shown in FIG. 6. The reflected beam is directed to an optical detector. This can be utilized in a one- or two-dimensional array. The "Y" coupler is sometimes referred to as a "Y branch" coupler (see, IEEE Spectrum, p. 58 (March 1986)). Similarly, a directional coupler can be used to combine the source and reflected beams (Id. at 58).

Figure 7:
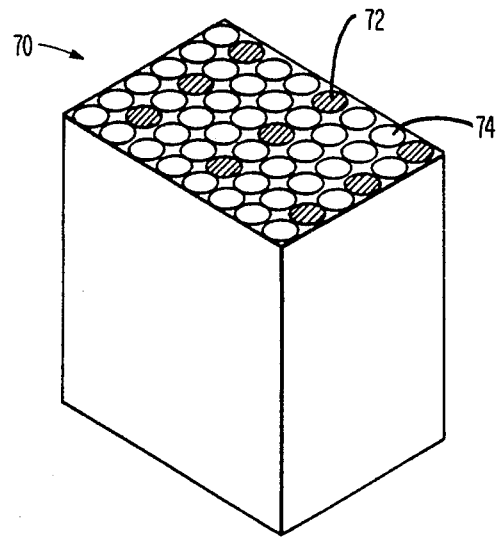
FIG. 7 shows a fiber bundle comprising source fibers (shaded) and receiver fibers.
Figure 8:
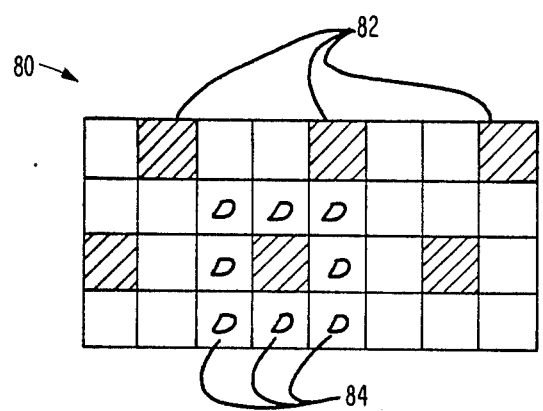
FIG. 8 shows a fiber arrangement format wherein each source fiber (which may also be a receiver fiber) is surrounded by receiver fibers to sample the reflected light.

When a two-dimensional (or linear) array is contemplated, several fibers (a bundle) may be incorporated into one radiation detecting element. As shown in FIG. 7, some fibers may be used as sources, while the other fibers are used as receivers. Polarizers may be used on the input and output. FIG. 8 shows a possible arrangement of source or source/receiver and receiver fibers in a fiber bundle. In this arrangement, each source element has a plurality of nearest receiver fiber neighbors (in this case there are eight neighbors). The reflected light can be sampled by all eight neighbors or some subset thereof. The receiver fibers can all be coupled to independent optical detectors or to only one optical detector.

The idea of a beam splitter (Y couplers, etc.) can also be employed with a mask scanned format. The purpose of the mask is to minimize optical cross talk between sources by ensuring adequate spatial separation between those sources. The mask moves in order to sample all points on the compression plate. If a two-dimensional source is used to illuminate a strip or an entire area, a mask with opaque areas will be needed. A virtual mask can be constructed with fiber optics by spatially separating the source fibers. The described reflection imaging devices can be incorporated into an optical CT scanner. Transmission CT images, reflection CT images, and composite CT image (using information from the first two images) could be reconstructed.

A significant fraction of the intensity of a collimated light beam (the primary beam) incident on a scattering and absorbing medium such as human tissue may be scattered one or more times prior to transmission or reflection out of the medium. The transmitted beam will be considered here since the techniques and principals to be described below can also be applied to the reflected beam. The transmitted beam intensity may thus include a collimated component $I_{tc}$ parallel to the incident beam and a scattered component $I_{ts}$.

The intensity of the transmitted collimated beam $I_{tc}$ may have two components: $I_{tc} = I_{pc} + I_{sc}$, where $I_{pc}$ is the unscattered primary collimated component, and $I_{sc}$ is the scattered collimated component comprising multiple-scattered photons aligned with $I_{pc}$. By determining and correcting for the magnitude of $I_{sc}$, the contrast of the resulting image, as well as the scan beam cross section, can be increased since the contribution to $I_{tc}$ from $I_{sc}$ is expected to grow (within limits) as the collimated beam cross section is enlarged.

If $I_{sc}$ is defined as the intensity of the transmitted scatter component at scatter angle $\theta = 0°$ (i.e., parallel to the collimated primary beam), such that $I_{sc} = I_{ts}(\theta = 0°)$, an acceptable approximation to $I_{sc}$ would be $I_{ts}(\theta)$ measured at an angle $\theta \approx$ small. If $I_{ts}(\theta)$ is measured at progressively smaller values of $\theta$, an asymptotic limit can be estimated for the case of $\theta \rightarrow 0°$ such that $I_{ts}(\theta) \approx I_{sc}$.

Alternatively, if the perimeter is not too large, the scattered intensity outside the immediate periphery at $\theta = 0°$ can be measured directly as an approximation for $I_{sc}$ since this component must be strictly due to scattering.

Figure 11:
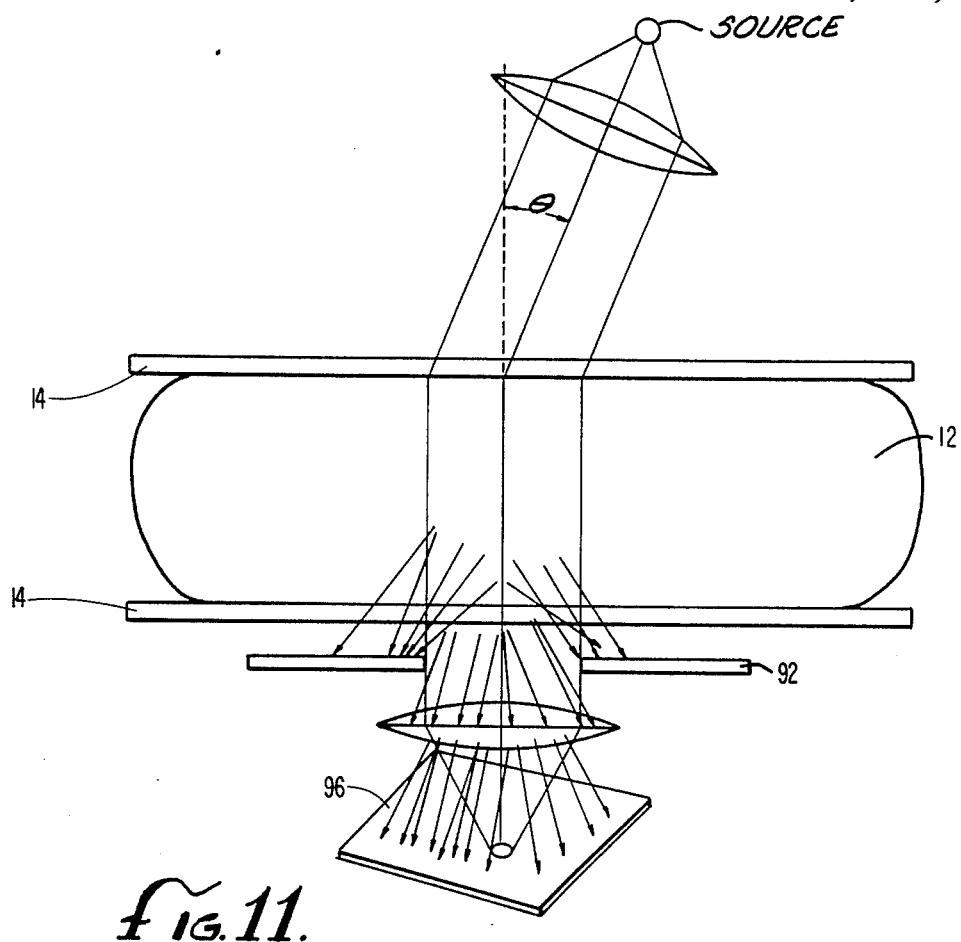
FIG. 11 shows a design for directly measuring scattered radiation using a beam oriented at angle $\theta \approx$ small.

Alternatively, as shown in FIG. 11 a second beam can be utilized to sample the same volume of tissue. However, this beam will have a divergence angle $\theta \approx$ small or be collimated and incident at angle $\theta \approx$ small. The collimated scatter component proportional to $I_{sc}$ (parallel to the first collimated beam) can then be measured directly.

Several techniques may be utilized in order to approximate $I_{sc}$ from measurements made inside the beam boundary. An angle sensitive collimator such as an optical fiber may be employed to aid in the determination of $I_{tc}$ and $I_{ts}(\theta)$.

The angle sensitive collimator is oriented to transmit only $I_{pc} + I_{sc}$. Then the collimator is tilted by an angle $\theta$ to allow passage of the beam component whose intensity is $I_{ts}(\theta)$. If $\theta$ is sufficiently small, then the intensity of scattered collimated component of the beam $I_{sc}$ will be proportional to $I_{ts}(\theta)$. It would be desirable to tilt the collimator and rotate it through 360° about the center of the beam.

An angle sensitive collimator array such as a fiber bundle could also be employed.

If an angle sensitive collimator transmits $I_{pc} + I_{sc} + I_{ts}(\theta)$ is employed, a lens of conventional or grin type could be used to focus $I_{pc}+I_{sc}$ through a blocking collimator and onto an optical receptor. By tilting the lens and blocking collimator arrangement, measurements of $I_{ts}(\theta)$ could be acquired.

Angle discrimination may be achieved by changing the position of a single detector so as to intercept all or part of the partially collimated transmitted beam containing $I_{tc}+I_{ts}(\theta)$. In the first position the detector is positioned such that the entire beam intensity $I_1=(I_{tc}+I_{ts}(74))$ will be detected. In the second position an air gap is introduced such that the detector receives substantially only the coaxial component of the beam whose intensity is $I_2=I_{tc}$. If the intensity of the beam as measured at position 2 is $I_2$, then $I_{ts}(\theta)=I_1-I_2$, and $I_{pc}=I_2-I_{ts}(\theta)=2I_2-I_1$.

A similar effect may be obtained using a fixed detector with a variable aperture (mechanical or electro-photonic). The detector and aperture are located such that $I_{tc}$ and $I_{ts}(\theta)$ fall on separate areas of the detector surface. A mechanical aperture can be varied, permitting the detector surface to measure either the intensity $(I_{tc}+I_{ts}(\theta))$ or $I_{tc}$. An electro optical aperture comprised of a central region and surrounding annulus which can be switched between transmissive and non-transmissive state, could permit the measurement of $I_{tc}$ and $I_{ts}(\theta)$ at separate times with one detector.

Alternatively, mirrors or fibers could be used to direct $I_{tc}$ and $I_{ts}(\theta)$ (assuming they are spatially separated) to two different detectors. A similar measurement can be obtained using a two dimensional detector array such as a CCD to record the intensities of the spatially separated components $I_{tc}$ and $I_{ts}(\theta)$ simultaneously.

Figure 9:
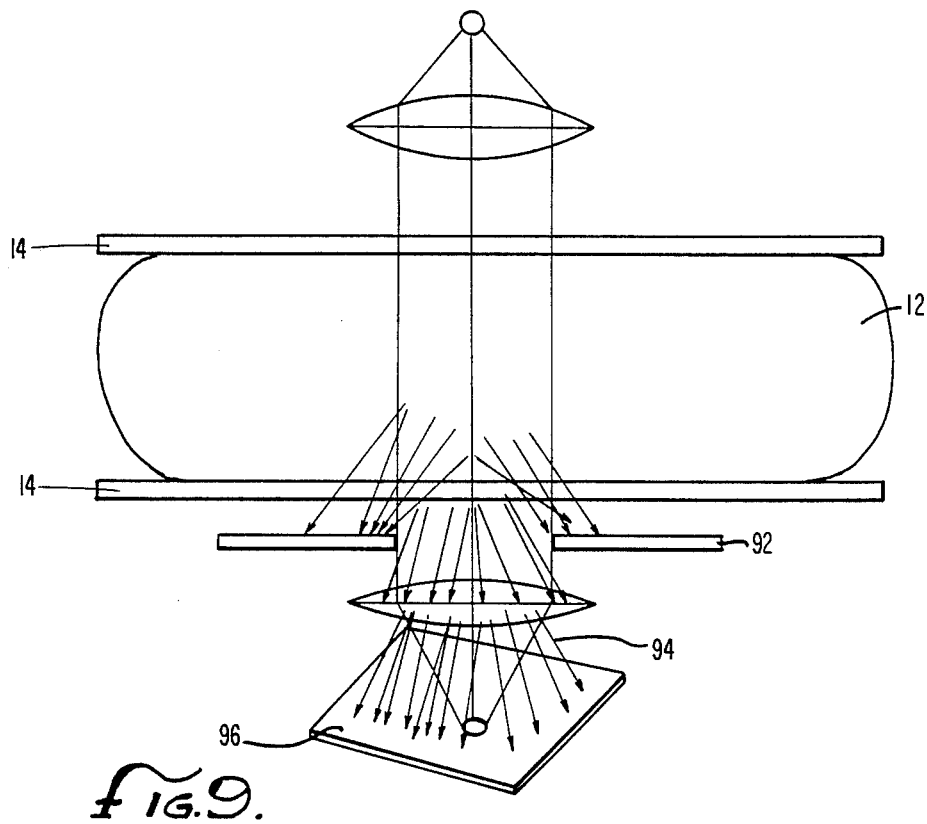
FIG. 9 shows a design for measuring coaxial and noncoaxial scattered radiation using a collimator, a lens and a two-dimensional detector.

As shown in FIG. 9 an air gap or air gap with a focusing lens may be used to spatially separate $I_{tc}=I_{pc}+I_{sc}$ from $I_{ts}(\theta)$. A two-dimensional detector could measure $I_{pc}+I_{sc}$ and $I_{ts}(\theta)$. Other means of separating $I_{tc}$ from $I_{ts}(\theta)$ could include narrow bandwidth, angle sensitive devices such as interferometric devices, diffracting gratings, and multilayer thin film designs which are highly transmissive (or reflective) at a given angle of incidence at a particular wavelength. These devices could be used as angle sensitive collimators in general. Likewise, for a polarized input beam, a polarizing prism or beam splitter could be employed to separate components.

A single beam or a number of beams can be imaged simultaneously. For example, an array of microlenses or tapered fiber optic elements or fibers with microlenses may provide a convenient two dimensional focusing system for high speed image acquisition. Depending on the arrangement of detectors and desired acquisition speeds, these angle sensitive devices (lenses, multilayer films, etc.) could be tilted, permitting acquisition of $I_{tc}$ and $I_{ts}(\theta)$ separately.

If the incident beam is polarized (polarization angle $\phi=0°$, then a polarizing filter may be used to remove a fraction of the scattered collimated component $I_{sc}$ present in the transmitted collimated beam. If the polarization vector is randomized for $I_{sc}$ (i.e. $I_{sc}$ has no memory of the initial polarization t direction), then an ideal polarized filter rotated at $\phi=90°$ to the incident beam polarization angle would transmit 50% of $I_{sc}$ while removing $I_{pc}$ entirely. In general, for transmitted scatter or backscatter radiation, a polarized filter can be utilized to evaluate the polarization state of the scatter radiation and perhaps advantageously remove an undesired component of the transmitted or backscattered beam. This polarizing filter can be absorptive (such as a polaroid ® polarizer material) or a polarization sensitive transmissive-reflective device such as an interferometer, a multilayer thin film, a polarizing prism, to name but a few.

Figure 10:
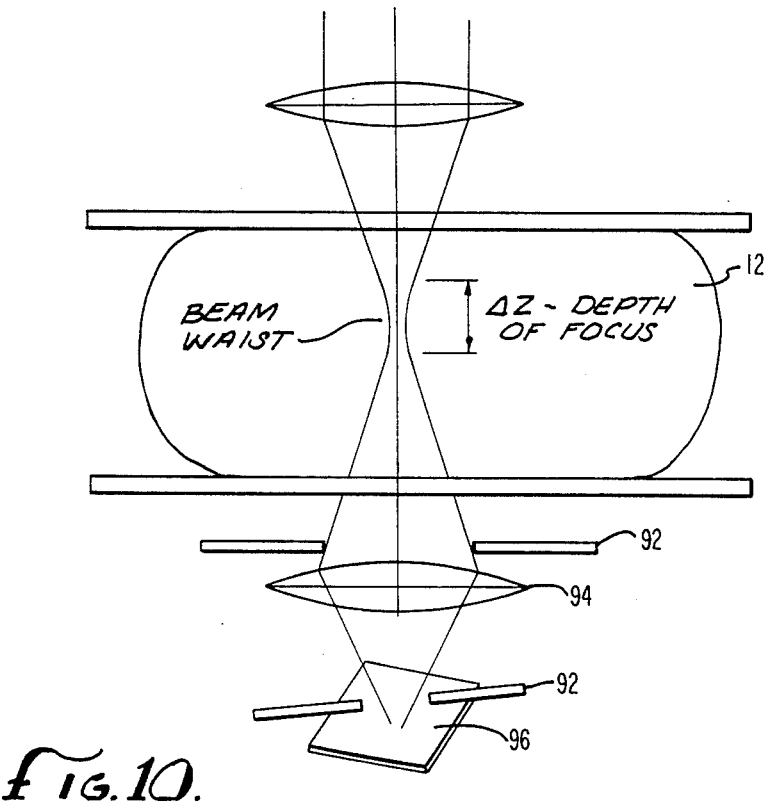
FIG. 10 shows a design for measuring coaxial and noncoaxial scattered radiation in tomography using a lens, a collimator and a detector.

As a result of the transmissive and reflective imaging apparatus and methods disclosed above, certain implications also arise in connection with transmissive or backscatter computed tomography. Scanning applications may occur in which optical CT is difficult to implement due to the thickness of the object or a troublesome geometry. Tomography could still be a desirable imaging format, but the surface might preferably be flattened or the surface contour followed. Useful information as a function of depth could be acquired if the object is scanned using a focused beam. Various optical devices including lenses, grin lenses, fiber with lens, mirrors, holographic and fresnel lenses may be used to focus the beam such that there is a well-defined depth of focus over a range $\Delta z$ measured with respect to the beam waist (see FIG. 10). Scanning the object permits a planar slice to be acquired with thickness and spatial resolution defined relative to the depth of focus $\Delta z$ and the beam waist, respectively. Multiple slices can be acquired by adjusting the beam waist location within the medium. Different sets of information can be acquired by measuring both the transmitted and backscattered beams. As described earlier, collimation techniques which include air gaps, fiber optics or light pipes, mechanical apertures, interferometric or diffraction techniques, masks, and polarizing filters can be employed to limit the magnitude, angular distribution and polarization state of detected scatter.

It may be advantageous to employ a focused, output optical system matched to the input focused optical system, maintaining a similar angular distribution between input and output beams. Using small angle correction techniques described previously, contributions to the transmitted focused beam due to multiple scattered photons can be estimated. It should be clear that the optical tomography technique described here can be utilized for industrial imaging as well as for the imaging of various regions of the body. A focused beam can also be utilized for conventional optical CT.

Thus, a high resolution imaging apparatus and method for approximating scattering effects is disclosed. While embodiments and applications of this invention have been shown and described, it would be apparent to those skilled in the art that many more modifications are possible without departing from the inventive concepts herein. The invention, therefore, is not to be restricted except in the spirit of the appended claims.

What Is Claimed Is:

1. An apparatus for obtaining improved tissue images using non-ionizing radiation of narrow bandwith comprising:
   a collimated source of non-ionizing radiation of relatively narrow bandwidth disposed such that radiation is incident on a sample of the tissue to be scanned,
   an optical detector disposed so as to detect radiation after transmission or reflection out of said tissue,
   a collimation device disposed between said tissue sample and said detector,
   and means for spatially separating a collimated component of said radiation from a scattered component of said radiation, said means being disposed between said collimation device and said detector.

2. The apparatus set forth in claim 1 wherein said radiation separation means comprise a focusing lens and an air gap.

3. The apparatus set forth in claim 1 wherein said collimation device disposed between said tissue and detector excludes the scattered component of said radiation, and further including a second collimated source of non-ionizing radiation of relatively narrow bandwidth which is tilted by a desired small angle before incidence on said tissue to be scanned, said detector being adapted to detect radiation passing through said tissue from said second radiation source in order to approximate a component of said first source of radiation due to multiple scattering.

4. The apparatus set forth in claim 1 further including a second source of non-ionizing radiation of relatively narrow bandwidth which produces a beam of known divergence relative to the first source at the entrance surface of said tissue to be scanned, said detector being adapted to detect radiation passing through said tissue from said second radiation source in order to approximate a component of said first source of radiation due to multiple scattering.

5. The apparatus set forth in claim 1 wherein the collimating component disposed between said tissue and said detector permits transmission of a beam with larger cross section than that of the unscattered component of the beam, and excludes the scattered component, and wherein the detector is disposed so as to measure the collimated beam intensities both inside and outside the perimeter of the unscattered beam cross section in order to approximate component of said source of radiation due to multiple scattering.

6. An apparatus for obtaining tomographic image slices of a tissue sample using non-ionizing narrow bandwidth radiation comprising:
   a focused optical source of non-ionizing radiation of relatively narrow bandwidth disposed such that radiation will be incident on a sample of tissue to be scanned,
   an optical detector disposed so as to detect radiation after transmission or reflection out of said tissue sample,
   a collimation device disposed between said tissue sample and the detector,
   and said focused source being translated so as to scan said tissue with best resolution at a given depth.

7. A method for reducing the contribution of multiple scattered photons to the detected signal from a collimated beam of non-ionizing radiation of relatively narrow bandwidth comprising the steps of measuring the intensity of the on-axis component of the beam, measuring the intensity of the beam at a slight off-axis angle and determining the intensity of the unscattered on-axis component of the beam.

8. A method for obtaining tomographic image slices of a tissue sample using non-ionizing radiation of relatively narrow bandwidth comprising the steps of scanning a sample of tissue by translating a focused optical beam through said sample, collimating the beam exiting said tissue sample and measuring the collimated exit beam with an optical detector.

9. A method for reducing the contribution of multiple scattered photons to the detected signal from a collimated beam of non-ionizing radiation of relatively narrow bandwidth comprising the steps of measuring the intensity of the on-axis component of the beam, introducing a second source of non-ionizing radiation of relatively narrow bandwidth, orienting the second source such that the beam therefrom has a known divergence relative to the collimated first source, measuring the intensity of the offaxis component of the second source and determining the intensity of the unscattered on-axis component of the first beam.

10. A method for reducing the contribution of multiple scattered photons to the detected signal from a collimated beam of non-ionizing radiation of relatively narrow bandwidth comprising the steps of permitting said beam to have a larger cross section than that of the unscattered component of the beam, measuring the intensities of the on-axis components of the beam inside and outside the perimeter of the unscattered beam and determining the intensity of the unscattered on-axis component of the unscattered beam inside the perimeter of the beam.

* * * * *

UNITED STATES PATENT AND TRADEMARK OFFICE
CERTIFICATE OF CORRECTION

PATENT NO. : 4,948,974

DATED : August 14, 1990

INVENTOR(S) : NELSON et al

Page 1 of 2

It is certified that error appears in the above-identified patent and that said Letters Patent is hereby corrected as shown below:

```
Column 2, line 54, insert --70-- after "bundle" and insert --72--
                   after "fibers",
          line 56, insert --74-- after "fibers",
          line 56, insert --80-- after "arrangement",
          line 57, insert --82-- after "fiber" (first occurrance),
          line 58, insert --84-- after "fibers",
          line 61, insert --92-- after "collimator" and insert
                   --94-- after "lens", and
          line 62, insert --96-- after "detector".
Column 3, line 8,  insert --10-- after "light",
          line 10, insert --12-- after "breast",
          line 11, insert --(not shown)-- after "breast",
          line 25, insert --14-- after "plates",
          line 39, insert --20-- after "beam" (first occurrence)
                   and insert --22-- after "beam" (second occurrence),
          line 49, insert --24-- after "plates",
          line 57, insert --30-- after "detector",
          line 58, insert --32-- after "splitter",
          line 60, insert --34-- after "unit",
          line 62, insert --36-- after "plate" (first occurrence),
          line 64, insert --38-- after "detector", and
          line 65, insert --40-- after "(plate B)".
Column 4, line 15, insert --42-- after "I" and insert --44--
                   after "II".
Column 5, line 36, insert --52-- after "array" and insert --14--
                   after "light",
          line 43, insert --60-- after "coupler", and
```

UNITED STATES PATENT AND TRADEMARK OFFICE
CERTIFICATE OF CORRECTION

PATENT NO. : 4,948,974

DATED : August 14 1990

INVENTOR(S) : Nelson et al

It is certified that error appears in the above-identified patent and that said Letters Patent is hereby corrected as shown below:

Column 5, line 46, insert --62-- after "detector".

Signed and Sealed this

Eighteenth Day of February, 1992

Attest:

HARRY F. MANBECK, JR.

Attesting Officer

Commissioner of Patents and Trademarks